(12) United States Patent
Deal et al.

(10) Patent No.: US 9,555,143 B2
(45) Date of Patent: Jan. 31, 2017

(54) INSTRUMENT DISINFECTION QUALITY METHODS AND DEVICES

(71) Applicant: UVAS, LLC, Charleston, SC (US)

(72) Inventors: Jeffery L. Deal, Charleston, SC (US); Phillip J. Ufkes, Sullivans Island, SC (US)

( * ) Notice: Subject to any disclaimer, the term of this patent is extended or adjusted under 35 U.S.C. 154(b) by 0 days.

(21) Appl. No.: 14/658,853

(22) Filed: Mar. 16, 2015

(65) Prior Publication Data
US 2015/0190539 A1 Jul. 9, 2015

Related U.S. Application Data

(63) Continuation-in-part of application No. 14/215,397, filed on Mar. 17, 2014, now Pat. No. 9,205,162.

(60) Provisional application No. 61/989,250, filed on May 6, 2014, provisional application No. 61/792,267, filed on Mar. 15, 2013.

(51) Int. Cl.
| | |
|---|---|
| A61L 2/00 | (2006.01) |
| G05B 1/00 | (2006.01) |
| A61N 5/00 | (2006.01) |
| G01N 23/00 | (2006.01) |
| A61L 2/10 | (2006.01) |
| A61L 2/28 | (2006.01) |
| A61L 9/00 | (2006.01) |

(52) U.S. Cl.
CPC .. *A61L 2/10* (2013.01); *A61L 2/00* (2013.01); *A61L 2/28* (2013.01); *A61L 9/00* (2013.01); *A61L 2202/14* (2013.01); *A61L 2202/15* (2013.01); *A61L 2202/24* (2013.01)

(58) Field of Classification Search
CPC .................................. A61L 2/00; A61L 2/0029
USPC .................... 422/24, 105; 250/455.11, 492.1
See application file for complete search history.

(56) References Cited

U.S. PATENT DOCUMENTS

| | | | |
|---|---|---|---|
| 5,637,877 A | 6/1997 | Sinofsky | |
| 6,656,424 B1 | 12/2003 | Deal | |
| 6,712,756 B1 | 3/2004 | Kura et al. | |
| 7,175,806 B2 | 2/2007 | Deal et al. | |
| 8,623,275 B2 | 1/2014 | Deshays | |
| 2007/0280852 A1 | 12/2007 | Skubal et al. | |
| 2008/0075629 A1* | 3/2008 | Deal | A61L 2/10 422/24 |
| 2008/0265179 A1* | 10/2008 | Havens | A61L 2/10 250/492.1 |
| 2010/0178196 A1 | 7/2010 | Garner | |

(Continued)

OTHER PUBLICATIONS

PCT International Search Report and Written Opinion, dated Aug. 11, 2014.

(Continued)

*Primary Examiner* — Monzer R Chorbaji
(74) *Attorney, Agent, or Firm* — B. Craig Killough; Barnwell Whaley Patterson Helms

(57) ABSTRACT

Devices and methods for defining a data set, referred to herein as a signature, for a particular device having interior channels. A baseline signature is established for the particular device while the particular device is known to be in a decontaminated condition. After use of the device and subsequent decontamination of the device, a signature for the particular device is determined and compared with the baseline signature to verify that the latter signature is within an acceptable range.

14 Claims, 6 Drawing Sheets

(56) References Cited

U.S. PATENT DOCUMENTS

2010/0178200 A1* 7/2010 Walker .............. A61K 41/0019
422/24
2012/0282135 A1 11/2012 Trapani

OTHER PUBLICATIONS

PCT International Search Report and Written Opinion, dated Jun. 30, 2015.

* cited by examiner

US 9,555,143 B2

INSTRUMENT DISINFECTION QUALITY METHODS AND DEVICES

Applicant claims the benefit of U.S. Provisional Application Ser. No. 61/989,250 filed May 6, 2014; this Application is a Continuation in Part of U.S. application Ser. No. 14/215,397 filed Mar. 17, 2014, which claims priority to U.S. Provisional Application Ser. No. 61/792,267, filed Mar. 15, 2013.

FIELD OF THE INVENTION

This invention relates to disinfection and cleaning devices and methods and is more particularly directed to qualify control methods and devices for instrument disinfection.

BACKGROUND OF THE INVENTION

The nature of bacteria acquired in the health care setting differs significantly from bacteria found in a community setting, primarily in their resistance to antibiotic therapy. Abundant evidence exists, however, that the hospital environment itself contributes to the problem by harboring virulent strains of bacteria, fungi, and viruses, and that many disinfection methods commonly used are ineffective and may actually spread contaminants. These contaminants are present on objects used in the health care setting, and in particular, on medical devices or instruments. These instruments must be decontaminated between uses.

Many medical devices are reusable after decontamination. Along with such materials pathogens and other contaminants are introduced. Endoscopy involves looking inside the body. Many of these devices have lumens and other channels or passages in which blood, tissue, and other materials are introduced during medical procedures. Decontamination of lumens and other channels and passages is critical, but also difficult due to access.

Endoscopes are non-exhaustive examples of such devices. Endoscopy is a common procedure in modern medical practices. Endoscopy involves the use of an endoscope, which is an instrument used to examine the interior of a hollow organ or cavity of the body. Endoscopes are inserted directly into an organ. Channels in endoscopes are used to transport medical instruments and materials, such as gasses and fluids. Tissue and fluids from the patient, and associated pathogens, are introduced into interior channels of the endoscope during such procedures. These devices must be decontaminated between uses.

Examples of such devices are flexible and rigid endoscopes. Endoscopes are used to examine and surgically manipulate the sinus cavities, upper and lower gastrointestinal tracts, lung fields, larynx, and intra-abdominal spaces. Endoscopes may have interior channels or conduits that are difficult to reach and disinfect. Relatively straightforward methods exist to disinfect endoscopes, although the working life of the endoscopes is lessened by washing due to chemical degeneration of components of the endoscope. An ongoing problem has been the reliable disinfection of endoscopes that have interior channels. Channels are used to inject liquid irrigants, suction, and to pass flexible instruments such as biopsy forceps. Interior channels and chambers have represented a challenge to infection control efforts.

Ultraviolet irradiation, particularly in the C bandwidth (2537 Angstroms), when given in adequate doses is lethal to all known pathogens. Microbes are uniquely vulnerable to the effects of light at wavelengths at or near 2537 Angstroms, due to the resonance of this wavelength with molecular structures. For the purposes of this document, the term UV-C is used for a wavelength of light being utilized for its germicidal properties, this wavelength being in the region of 2537 Angstroms.

The United States Food and Drug Administration and the United States Center For Disease Control and Prevention define disinfection as the use of a chemical procedure that eliminates virtually all recognized pathogenic microorganisms but not necessarily all microbial forms (e.g., bacterial endospores) on inanimate objects. There are three levels of disinfection: high, intermediate, and low. High-level disinfection kills all organisms, except high levels of bacterial spores, and is effected with a chemical germicide cleared for marketing as a sterilant by the Food and Drug Administration. Intermediate-level disinfection kills mycobacteria, most viruses, and bacteria with a chemical germicide registered as a "tuberculocide" by the Environmental Protection Agency (EPA). Low-level disinfection kills some viruses and bacteria with a chemical germicide registered as a hospital disinfectant by the EPA. For the purposes of this document, "disinfection" includes all three of these levels.

SUMMARY OF THE INVENTION

The present invention provides devices and methods for defining a data set, referred to herein as a signature, for a particular medical device or other instrument having interior channels. A baseline signature is established for the particular device while the particular device is known to be in a decontaminated condition. After use of the device and subsequent decontamination of the device, a signature for the particular device is determined and compared with the baseline signature to verify that the latter signature is within an acceptable range. The device may be a medical device, and may be an endoscope.

DESCRIPTION OF PREFERRED EMBODIMENTS

Figure 1:
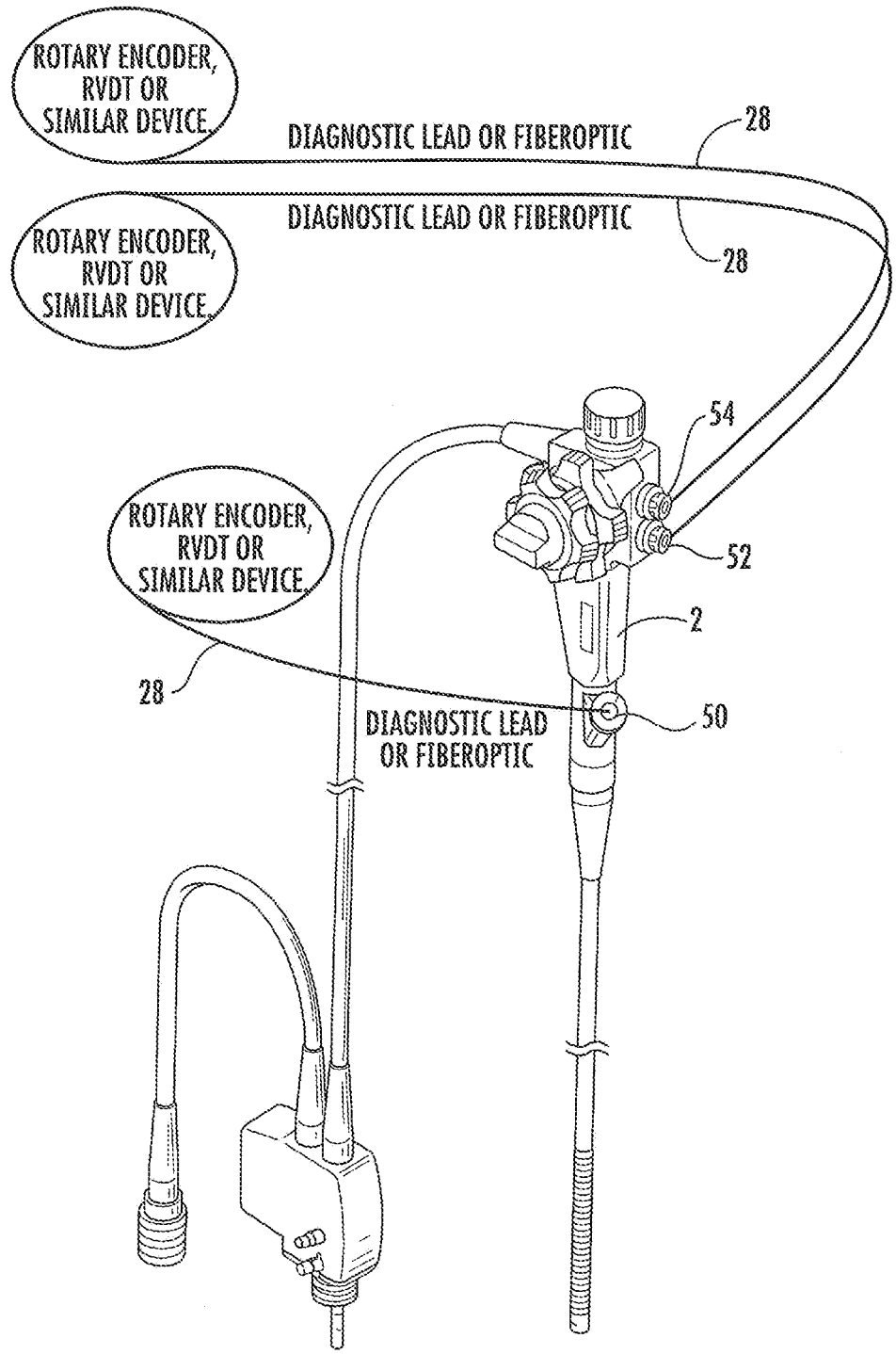
FIG. 1 is a perspective view of a medical device having interior channels.

FIG. 1 shows a medical instrument or device 2, and specifically, an endoscope having interior channels. In the exemplary embodiment shown in FIG. 1, the device has three interior channels, each having a port 50, 52, 54 that opens to an exterior of the device. The multiple channels of the device permit simultaneous use of a camera, one or more medical devices for carrying out a procedure, and/or one or more channels for delivering or removing fluids or gases from the body of a patient.

When the medical device 2 is used in a medical procedure, the channels become contaminated with tissue and/or fluids from the patient. After use, the medical device 2 is decontaminated by known decontamination methods. Decontamination methods include exterior decontamination, as well as decontamination of interior channels.

According to one embodiment of the present invention, an energy emitter is progressively transported through each of the channels. Energy is emitted from the emitter as it progressively moves through the channel. Energy emission is continuous or substantially continuous. Energy is reflected back to a receiver that is also progressively transported through the channel, and preferably, simultaneously with the emitter, and at the same rate as the emitter, so as to measure reflectance substantially continuously along the length of the channel.

The receiver may be positioned relative to the emitter to receive reflected energy emitted and then reflected from interior surfaces of the channel through which the emitter travels. Reflectance is measured periodically, and recorded, so that there is a reflectance measurement that corresponds to a location of the receiver within the channel. It is preferred that the rate of progression of the emitter and receiver, and the number of measurements taken, is such that reflectance is measured substantially continuously for the entire length of the channel. For example, for an emitter that is transported through the channel at the rate of 2 centimeters per second, 120 reflective measurements per second are taken so that a reflective measurement is taken for each 1/60 centimeter of travel. It is preferred that a reflective measurement is taken each 1/30 to 1/90 centimeter of travel.

Figure 2:
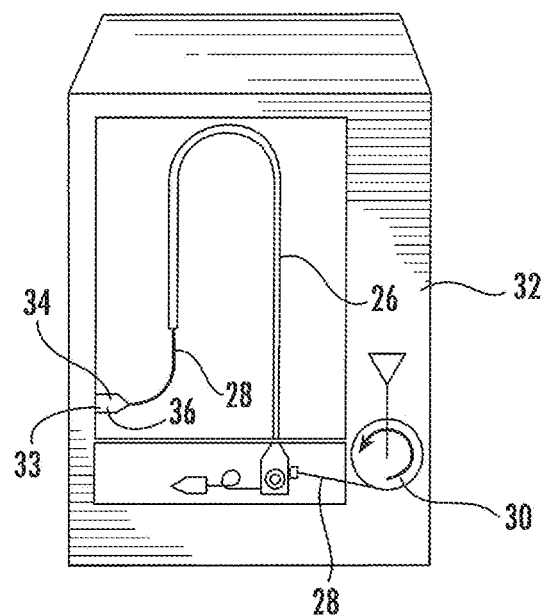
FIG. 2 is a front elevation of an exemplary device for producing disinfection and/or disinfection quality control according to an embodiment of the invention.

In one embodiment, an endoscope is placed within a housing. FIG. 2. A cable 28 conveys an emitter and receiver that communicate with a microcontroller 23. The emitter and receiver may communicate with an energy source and the microcontroller by a conductor. In a preferred embodiment, the emitter and receiver communicate with an energy source and the microcontroller by fiber optic material.

Figure 3:
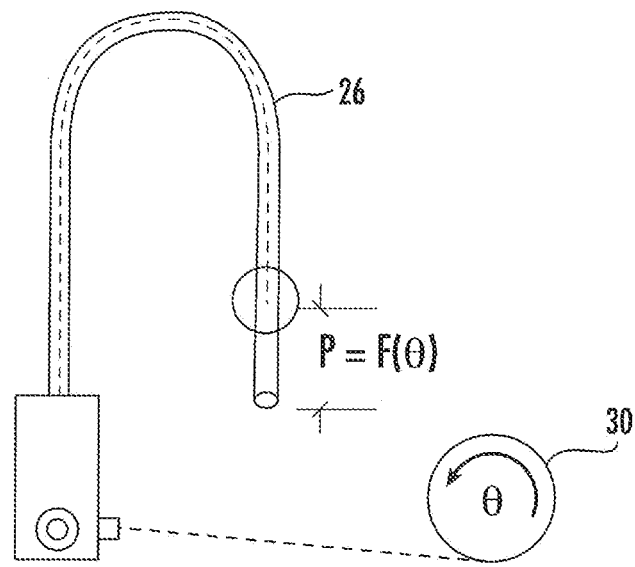
FIG. 3 is an isolation of components of a device for disinfection quality control according to an embodiment of the invention.

Components of FIG. 2 are shown in isolation in FIG. 3. As shown in FIG. 3, the position of the receiver is a function of the angular position of the velocity-controlled withdrawal device 30. Reflected energy from the emitter is received by the receiver at multiple positions and recorded. This process is performed, and reflectance data recorded when a specific device that is known to have acceptable levels of decontamination within its channels. A new endoscope, after decontamination, but prior to use, is an example. The first time that the process is performed for a known decontaminated channel may be used to determine a baseline signature for that specific channel, and may be repeated for each channel of a device to establish a baseline signature for the specific device. Reflectance as a function of position in the channel establishes the baseline signature for a known acceptable decontaminated device.

The baseline signature for the device is recorded and stored, for example, by serial number of the device. In one alternative, the device may be assigned a particular code. The serial number or other code is an identifier, which may be a barcode or QR code attached as a tag or label to the device, and which is capable of being read by an optical scanning device.

In a preferred embodiment, after the specific device, such as endoscope 2, is used, it is decontaminated by known processes. The process described above is preferred to be performed at the same energy emission levels and type of energy used in determining the baseline signature. Reflectance for the same locations along the length of the channels is measured and stored. The subsequent or later signature obtained from the decontaminated device is compared with the baseline signature for that specific device. Tolerance limits, based upon the baseline signature, are established. The tolerance limits provide acceptable decontamination ranges after subsequent use and decontamination.

Figure 4:
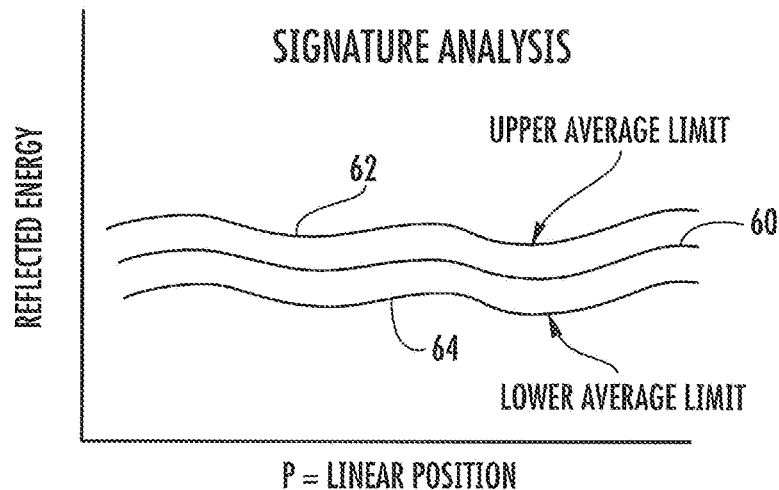
FIG. 4 is a graph demonstrating energy reflectance measurements at positions or locations of interior channels of an instrument known to be acceptably decontaminated.
Figure 5:
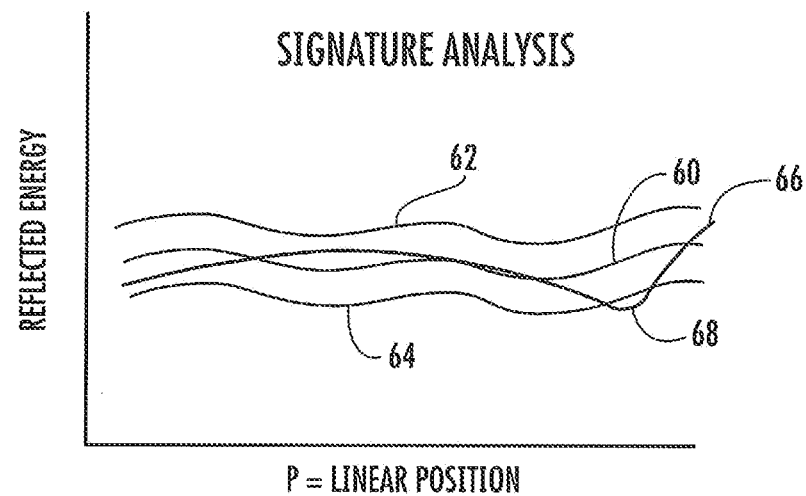
FIG. 5 is a graph demonstrating comparative energy reflectance measurements at positions or locations of interior channels of an instrument after use and decontamination of an instrument.

The comparison process according to an embodiment of the invention is demonstrated graphically in FIG. 4 and FIG. 5. The center line 60 of each graph represents the base line signature for a specific channel of a specific device that is known to be within acceptable decontamination limits, such as a new and unused endoscope after decontamination. An upper limit 62 and a lower limit 64 may be established around the baseline signature that represent acceptable deviations from the baseline signature 60. In most cases deviations from the baseline signature will by indicated by lower reflected light levels.

FIG. 5 shows a comparison of a later signature taken from the same device after use and decontamination. The reflected energy data is compared for each location or position within the channel. Reflectance after decontamination is demonstrated by line 66 of FIG. 5. The latter signature is generally within tolerance, but deviates at a lower limit of reflectance for a location, or linear position 68, along a channel. The signature comparison indicates that for a position of the channel, reflectance is outside the established specification, thereby indicating the possibility that foreign material present in the channel that has not been removed by the decontamination process.

The comparison process, according to the invention, not only indicates that the foreign material may be present and causing a deviation in reflection, but further, the process provides the specific location of the foreign material that may be causing the deviation. The channel may be subjected to the decontamination process a second time, or otherwise repeated as necessary, and specific focus may be given to cleaning and decontaminating the location that caused the deviation.

If the same reflectance data is obtained after a second attempt at decontamination, the process may indicate a damaged channel. This will especially be true if the second attempt at cleaning and decontamination does not yield at least marginal improvement. Marginal improvement may indicate some efficacy in subsequent decontamination or cleaning, but that cleaning is still inadequate. If less than marginal improvement has occurred, and the second signature is substantially the same as the first signature after decontamination, then physical damage to the channel may have occurred.

In one embodiment, the cable or fiber optic has a camera or lens fitted thereon. In the event that the latter signature shows a deviation from permitted tolerances, the camera can assist in determine the cause of the deviation by visually inspecting the problem location of the channel.

FIG. 2 shows a housing for an embodiment of the device. The housing 32 is preferred to be formed of a metal that is easy to clean, such as stainless steel or powder coated steel. The device may be capable of floor or wall mounting, according to the user's preference, and according to the overall size of the instrument or device to be decontaminated or measured for quality according to the process of the invention.

In one embodiment, a microcontroller system 23 provides energy to the emitter. The microcontroller may read signals from the energy receiver, and store data interpreted from signals transmitted by the receiver that correlate to a position in a channel of the device or instrument.

In use, objects, such as medical devices, which may be endoscopes 22, may be placed into the interior of the cabinet 32. The use of an enclosure such as the cabinet is not required, but is preferred to maintain a sufficiently sterile device after decontamination. In some embodiments, decontamination takes place in the cabinet, with the quality control process of the present invention performed without removing the medical device or channel 26 from the cabinet.

In an embodiment shown, a cable 28 is present in the cabinet. The cable comprises one or more energy emitters, which may be one or more light emitting diodes (LEDs), and preferably, one or more receivers that detect and measure, or transmit, reflected energy emitted by the emitter(s) and reflected at positions of the interior channels. After placement of the instrument such as an endoscope into the cabinet 32, and prior to activation of the UV-C emitters, the user inserts the cable 28, through interior channels of the endoscope. For demonstration purposes of this specification, a channel 26 is shown in isolation. The receiver is tuned to measure the intensity of, and total dosing of, radiant energy at the appropriate bandwidth for the form of energy that is emitted in the channel.

The radiant energy in the form of UV-C radiation may be emitted by one or more LEDs located at the end of the cable in one embodiment. The cable may be formed of an elongated material that will transport the emitter(s) and the receiver through the channel, and provide current to the LED and the receiver, and a signal from the receiver to the device as described herein for controlling the velocity of withdrawal of the cable. The cable may comprise fiber optic material having that will transmit energy to be emitted, and a signal for reflected energy received by the receiver.

Figure 8:
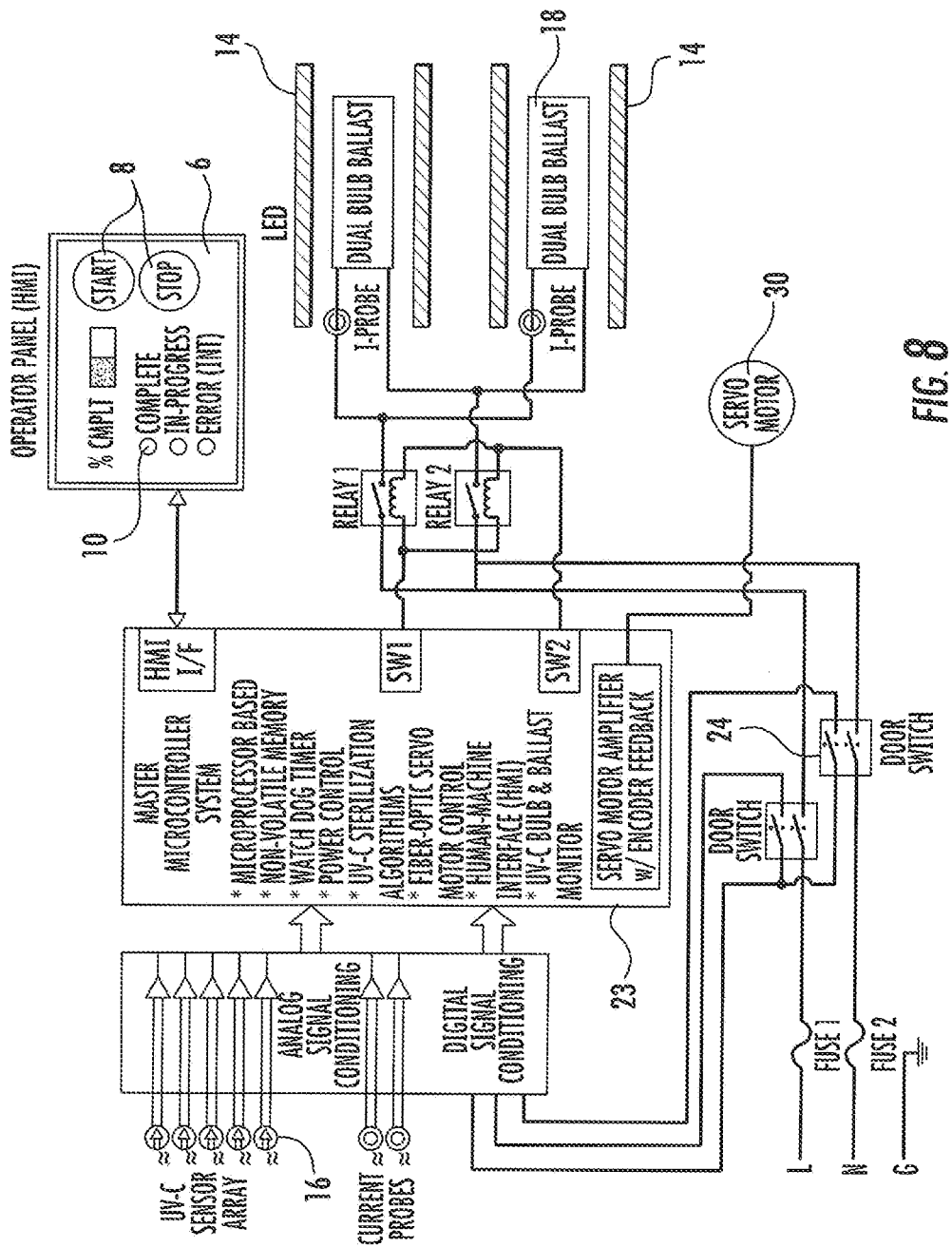
FIG. 8 is a schematic of an embodiment of the device according to the invention.

In one embodiment, reflected radiation or other energy received by the receiver(s) is read by the microcontroller system. The microcontroller controls the rate of withdrawal of the cable from the endoscope channel by a velocity-controlled withdrawal device 30. FIG. 8.

The microcontroller system may determine the level of reflected energy at each location of each channel of each particular device or instrument, and store the information according to an identifier for the particular device or instrument, with the information used for later comparison according to the invention. Alternatively, the microcontroller may transmit the channel reflectivity information to another processor for calculation and/or storage.

In one embodiment, an energy emitting LED 33 and a receiver 34 are positioned at the end of the cable 28. The receiver transmits and/or measures reflected energy emitted by the LED. A barrier that does not permit emitted energy or radiation to pass through may separate the emitter from the receiver so that the receiver receives reflected radiation but does not receive directly emitted energy or radiation. The structure and arrangement of the emitter and the receiver may otherwise be such that the receiver does not directly receive emitted energy or radiation.

Figure 7:
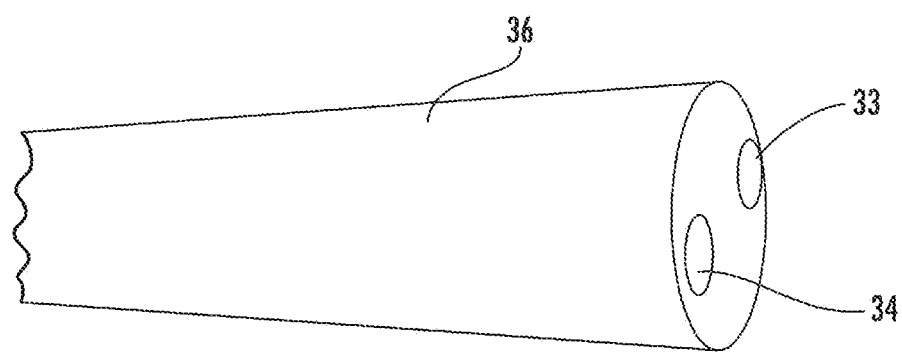
FIG. 7 shows another embodiment of an exemplary energy emitter and receiver that may be fitted to a lead that is progressively pulled through a channel of a device.

FIG. 7 shows an exemplary embodiment of an energy emitting LED 33 and a receiver 34 located in a terminal housing 36. The terminal housing is positioned at the end of the cable 28. The receiver is recessed in the terminal housing so that the receiver receives reflected energy, but does not receive direct energy emission from the emitter 33 that is positioned adjacent to the receiver. Reflected energy received by the receiver 34 is read by the microcontroller system, which controls the rate of withdrawal of the terminal housing and attached cable from the endoscope channel with the velocity-controlled withdrawal device 30, which may be a servo motor.

LEDs that are connected to a cable may be used in combination with fiber optic. The size of the channel and the material that forms the channel impacts the properties of the emitter and the specific type of energy that is emitted. LEDs may be larger and capable of providing more energy than fiber optic alone. The receiver that is local to the emitter will also be sized appropriately to the channel of the medical device. Alternatively, the cable may contain multiple emitters, such as multiple LEDs, and multiple receivers to accomplish measured reflectivity.

The cable to which the emitter is attached for positioning the emitter through the channel according to this embodiment may also be used to cool the emitter, especially in cases where substantial energy is emitted by the device. For example, the cable may comprise a lumen through which cool air is transmitted to cool an emitter such as an LED. The cable may comprise conductive materials, which may be metal, such as copper, to conduct heat. The conductive material may also conduct current for powering the emitter, which may be one or more LEDs.

After an appropriate delay to allow a steady-state output, the microprocessor calculates the rate of withdrawal of the cable needed to properly measure reflectivity of the channel being treated. The controlled withdrawal device begins to extract the cable at the calculated rate.

The controlled withdrawal device may comprise a geared velocity controlled motor connected to a rubberized soft pulley system. The controlled withdrawal device is designed to pull the cable at a reproducible and controlled speed without damaging the cables. The cable is fed into a coiling chamber located above the light source. The rate of withdrawal of the cable is controlled by the microprocessor and so that later measurements are taken under equivalent functional conditions as those pursuant to which the baseline signature is taken.

Figure 6:
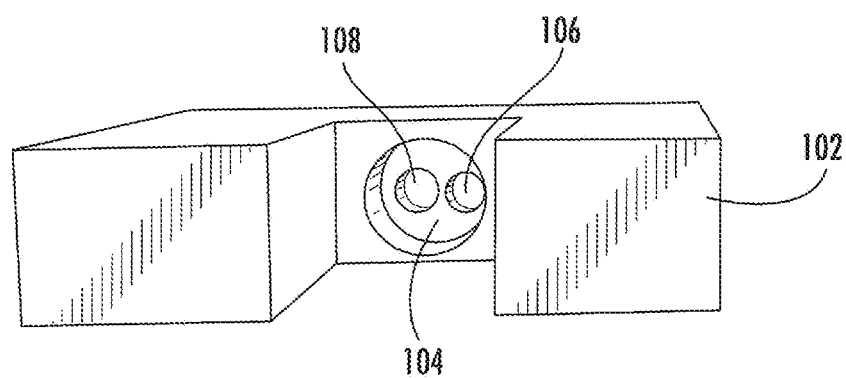
FIG. 6 is an exemplary energy emitter and receiver that may be fitted to a lead that is progressively pulled through a channel of a device.

In one embodiment, one or more emitters and one or more receivers are recessed into a terminal housing 102 in FIG. 6. One end of the cable 28 is inserted into larger recess 104. One or more receiver(s) 106 and one or more emitters 108 may be positioned inside of the smaller recesses. The receiver(s) read reflected energy that is transmitted through the channel.

Energy emissions from the emitter as provided by the device may be chosen from bandwidths that include visible light or ultraviolet radiation or other bandwidths that may be emitted, received and measured as described herein. The same bandwidth will be used for setting the baseline signature as for subsequent testing. If disinfection is achieved using UV-C radiation in the channels, UV-C may be the preferred bandwidth for the quality control method described herein. Disinfection and quality measurement in such cases may occur simultaneously or substantially simultaneously.

What is claimed is:

1. A quality control method for medical devices, comprising the steps of:

exposing a plurality of surface positions located in an interior of a medical device to energy emitted from an energy emitter after subjecting the medical device to a cleaning process;

measuring energy reflected from each surface position of the plurality of surface positions of the medical device and recording the energy reflected from each surface position of the plurality of surface positions of the interior of the medical device, wherein the reflected energy measured and recorded at each surface position of the plurality of surface positions produces a set of data points, wherein each of the data points corresponds to energy reflectivity from one of the surface positions of the plurality of surface positions, and wherein the data points produce a signature for the condition of the medical device after cleaning;

establishing a baseline signature, wherein the baseline signature is established by a second set of data points of energy reflectivity for each surface position of the plurality of surface positions located in the interior of the medical device for a known clean and properly functioning medical device;

comparing the signature for the condition of the medical device after cleaning to the baseline signature;

determining cleanliness and functioning of the medical device by the variance of the signature of the medical device after cleaning from the baseline signature.

2. The quality control method for medical devices of claim 1, comprising the additional steps of providing an identifier for the medical device, the baseline signature and the signature, and matching the identifier the medical device and the baseline signature and matching the identifier to the baseline signature and to the signature prior to comparing the baseline signature to the signature.

3. The quality control method for medical devices according to claim 1, wherein the energy emitter is progressively transported relative to the medical device to sequentially expose each surface position the plurality of surface positions of the interior of the medical device to energy emitted from the energy emitter, and measuring energy reflected from each surface position of the plurality of surface positions of the medical device at intervals as the energy emitter is progressively transported relative to the medical device, and recording the energy reflected from each surface position of the plurality of surface positions of the medical device at each interval to produce a signature for the medical device.

4. The quality control method for medical devices according to claim 1, wherein the energy emitted by the energy emitter is ultraviolet radiation.

5. The quality control method for medical devices according to claim 1, comprising the additional steps of providing a unique identifier for the medical device, the baseline signature and the additional signature, and matching the unique identifier to the medical device and the baseline signature and matching the unique identifier to the baseline signature and the additional signature prior to comparing the baseline signature to the signature, wherein the unique identifier is a machine readable code that is associated with the medical device.

6. The quality control method for medical devices according to claim 1, further comprising the step of establishing a tolerance limit for the signature prior to comparing the baseline signature to the signature.

7. The quality control method for medical devices according to claim 1, wherein the interior of the medical device comprises an interior channel, and the plurality of surface positions are located within the interior channel of the medical device.

8. The quality control method for medical devices according to claim 1, wherein the energy emitter is progressively transported through the interior of the medical device and the reflected energy measured and recorded at each surface position of the plurality of surface positions produces a set of data points.

9. A quality control device, comprising:

an energy emitter;

an energy receiver;

a conveyance device constructed and arranged to progressively convey the energy emitter and energy receiver through an interior lumen of a medical device; and a controller constructed to measure and record energy received by the energy receiver as a function of positon within the interior lumen of the medical device;

wherein the controller is constructed and arranged to establish a decontamination signature for the medical device by exposing a plurality of surface positions located in the interior lumen of the medical device to energy emitted from the energy emitter and measuring energy reflected from each surface position of the plurality of surface positions of the interior lumen of the medical device and recording the energy reflected from each surface position of the plurality of surface positions of the interior lumen of the medical device, wherein the reflected energy measured and recorded at each surface position of the plurality of surface positions produces a set of data points, wherein each of the data points corresponds to energy reflectivity from one of the surface positions of the plurality of surface positions, and wherein the data points produce the decontamination signature for the condition of the medical device.

10. A quality control device as described in claim 9, wherein the energy emitter and the energy receiver are mounted at an end of the conveyance device.

11. A cleaning quality control device as described in claim 9, wherein the energy emitter periodically emits energy that is directed to surfaces of the interior lumen of medical device as the medical device is transported though the interior lumen of the medical device, and wherein the energy receiver receives energy that is reflected from surfaces of the interior lumen of the medical device.

12. A quality control device as described in claim 9, wherein the conveyance device comprises a cable, and the cable comprises fiber optic material through which energy is transmitted and from which energy is emitted.

13. A quality control device as described in claim 9, wherein the energy emitter comprises a light emitting diode.

14. A quality control device as described in claim 9, wherein the conveyance device comprises a velocity controlled motor.

* * * * *